United States Patent
Ito

[11] 4,162,827
[45] Jul. 31, 1979

[54] WIDE ANGLE OBJECTIVE FOR OPHTHALMOSCOPIC INSTRUMENT

[75] Inventor: Yuji Ito, Chigasaki, Japan

[73] Assignee: Canon Kabushiki Kaisha, Tokyo, Japan

[21] Appl. No.: 802,877

[22] Filed: Jun. 2, 1977

[30] Foreign Application Priority Data

Jun. 9, 1976 [JP] Japan .................................. 51/67521

[51] Int. Cl.² ............................................. A61B 3/14
[52] U.S. Cl. ...................................... 351/7; 350/234; 351/13; 351/16; 354/62
[58] Field of Search .................... 351/7, 13, 16, 6; 354/62; 350/234

[56] References Cited

U.S. PATENT DOCUMENTS

| | | | |
|---|---|---|---|
| 1,293,086 | 2/1919 | Graf | 350/234 |
| 3,536,379 | 10/1970 | Knetsch | 350/234 X |
| 3,914,032 | 10/1975 | Takano et al. | 351/7 |

*Primary Examiner*—Paul A. Sacher
*Attorney, Agent, or Firm*—Toren, McGeady and Stanger

[57] ABSTRACT

An ophthalmoscopic camera with an achromatic objective arranged on a common optical axis of an image forming lens in front of a photographic film and adapted to project a ring-shaped bundle of illuminating light rays onto the cornea of an eye to be photographed as the illuminating light rays come from a light source through a relay lens after reflection from an apertured mirror positioned between the objective and the image forming lens at an angle with the optical axis thereof. For an increase in the angle of view, the objective is constructed in the form of a biconvex triplet consisting of a forwardly convex negative meniscus lens, an equi-convex lens and a rearwardly convex negative meniscus lens with its four refracting surfaces so configured and so separated that a beam of image forming rays passing through a central aperture of the illuminating mirror to the film can be made free from disturbing light reflections from these four lens surfaces by use of a single black spot positioned at a point between the light source and the mirror in coaxial relation thereto.

7 Claims, 3 Drawing Figures

WIDE ANGLE OBJECTIVE FOR OPHTHALMOSCOPIC INSTRUMENT

BACKGROUND OF THE INVENTION

This invention relates to ophthalmoscopic instruments, and more particularly to a wide angle achromatic photographic objective for use in such ophthalmoscopic instruments.

In conventional ophthalmoscopes and eye-fundus cameras, a large proportion of the objectives are formed as a positive meniscus lens convex toward an object (human eye). With this type objective, however, the angle of view has to be limited to about 30 degrees or less, or otherwise a substantially lowered picture quality will be resulted.

To increase the angle of view up to about 45 degrees, the objective preferably takes a biconvex form. When a chromatic correction is required, the biconvex objective is generally designed to have a cemented surface or surfaces. This gives rise to introduction of disturbing reflections from the cemented surface or surfaces.

SUMMARY OF THE INVENTION

A primary object of the present invention is to increase the angle of view of an achromatic photographic objective for use in an ophthalmoscopic instrument.

A secondary object is to provide a wide angle achromatic objective with the cemented surfaces formed therein to a configuration suitable for eliminating the undesirable light reflected from the cemented surfaces as the illuminating light rays are projected through the objective to the cornea of an eye to be examined.

According to the present invention, the objective is constructed in the form of a triplet consisting of, in the direction in which the image forming rays enter, a negative meniscus lens convex toward the eye, a biconvex lens, and a negative meniscus lens concave toward the eye. By employing the biconvex form for the central constituent lens in the triplet, it is made possible to eliminate all the disturbing light reflections from the cemented surfaces as well as from the front and rear surfaces by limiting the necessary number of light obscuring spots to only one as arranged in the path of illuminating light rays.

DESCRIPTION OF THE PREFERRED EMBODIMENT

Figure 1:
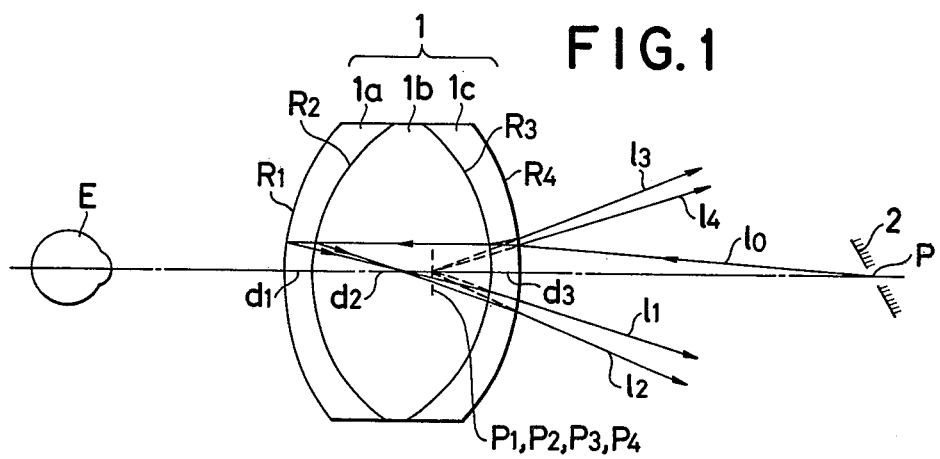
FIG. 1 is a block diagram of one embodiment of an achromatic photographic objective according to the present invention with geometrical illustration of the effect on elimination of the disturbing reflections from the various surfaces thereof.
Figure 2:
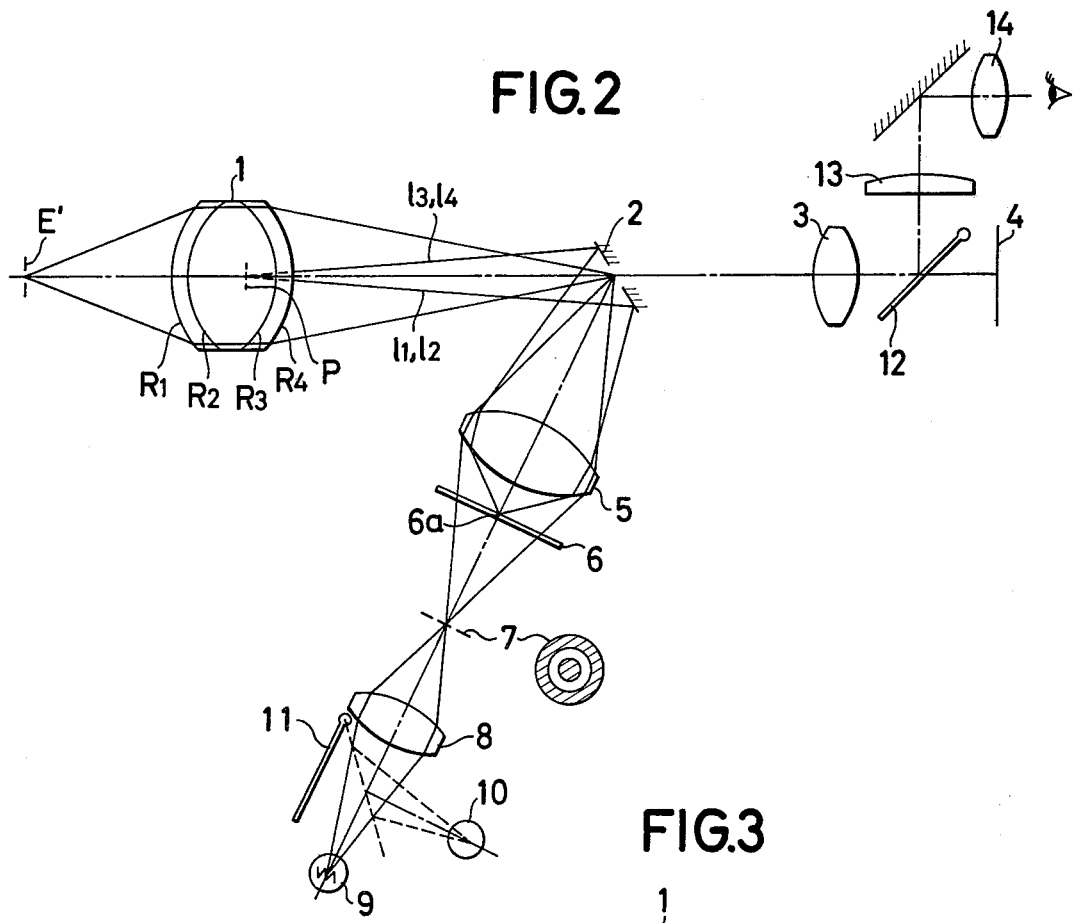
FIG. 2 is a schematic sectional view of an ophthalmoscopic camera with the objective of FIG. 1.

In FIGS. 1 and 2 and especially FIG. 2, there is shown an ophthalmoscopic camera for photographing the fundus of an eye E with its pupil indicated at E'. The camera includes an achromatic photographic objective 1 and an image-forming lens 3 arranged along a common optical axis in starting from the object end in front of a photographic film 4. Positioned between the objective 1 and the image forming lens 3 is an apertured mirror 2 inclined at an angle to the optical axis with an aperture disposed at its center coincident to the optical axis. The mirror 2 constitutes part of an illuminating optical arrangement which further includes a relay lens 5 adapted to produce an image of a ring-shaped patch 7 on the mirror 2, a condenser lens 8 positioned behind the path 7 in optically alined relation thereto for selectively forming an image of either one of two light sources, namely, a filament coil of an incandescent lamp 9 and an arc of a flash-tube 10 on the path 7. A mirror 11 in the illuminating optical arrangement is pivotable between an illustrated position where the incandescent lamp 9 is selected for visual observation of the ocular fundus through a viewfinder optical system, and a position indicated by a dashed line where the flash-tube 10 is selected for the exposure of the film 4. The viewfinder optical system comprises a reflex mirror 12 movable between a viewing position illustrated and a non-viewing position, a field lens 13, and an eye-piece 14. When the mirror 12 is in the viewing position, a final image of the ocular fundus is formed on the field lens 13 and can, therefore, be viewed by an eye of an observer looking through the eye-piece 14. It is to be noted here that instead of using the eye-piece 14 a collective lens may be used in combination with a pick-up tube with its image receiving surface being position in coincidence with the focal plane of the collective lens, so that an image of the ocular fundus is displayed on the Braun tube.

With this illuminating optical arrangement, it is possible to illuminate an annular zone of the pupil E' while the central portion remains unilluminated, as the objective 1 is adapted to project a final image of the ring-shaped patch 7 on the plane of the pupil E'. The image forming rays reflected from the retina and emerging from the pupil E' are collected by the objective 1 to form an intermediate image of the retina in front of the illuminating mirror 2. The size of the aperture of the illuminating mirror 2 is adjusted so that only that portion of the emergent rays from the pupil E' which passes through the unilluminated central portion thereof is allowed to pass through the aperture of the illuminating mirror 2. That portion is then focused by the image forming lens 3 on the film 4, provided that the mirror 12 is in the non-viewing position. An image of the fundus of the eye E is thus recorded on the film 4.

The illuminating light rays are incident on the front and rear surfaces $R_1$ and $R_4$ respectively in a direction opposite to that of the image forming rays. Hence a certain fraction of the illuminating rays is reflected from the rear surface $R_4$ so they diverge, and an additional fraction is reflected from the front surface $R_1$ so they converge. Both serve as disturbing incident light on the film 4. It is known that such disturbing light reflections can be eliminated, as, for example, disclosed in Japanese Patent Application Publication No. Sho 44-8406 and No. Sho 47-44645. However, no care has been taken of the disturbing reflections from the cemented surface or surfaces in the achromatic objective.

FIG. 1 shows one embodiment of the photographic objective according to the present invention the lens is constructed in the form of an achromatic triplet 1 consisting of a negative meniscus lens 1a convex toward the eye E to be photographed, a biconvex lens 1b, in this instance, equiconvex lens, and a negative meniscus lens 1c concave toward the eye E cemented at their adjoining surfaces. The material of the two negative meniscus lenses 1a and 1c has a higher index of refraction and a lower Abbe number than those of the material of the positive lens 1b.

In order to produce a beam of image forming light rays free from disturbing incident light rays between the objective 1 and the illuminating mirror 2, specific requirements are set forth as follows. Assuming now that a light ray, $l_0$, emanating from a point P on the central plane of the aperture of the illuminating mirror 2 impinges on the objective 1, four different virtual image points $P_1$, $P_2$, $P_3$ and $P_4$ are formed at different positions within the body of the objective by respective reflected rays, $l_1$, $l_2$, $l_3$, and $l_4$, from the respective surfaces $R_1$, $R_2$, $R_3$ and $R_4$ after the necessary successive refractions at the incident surfaces. In order to eliminate the four reflected rays, therefore, it is necessary to provide four black spots in the illuminating optical arrangement at respective positions conjugate to those of the virtual image points $P_1$ to $P_4$. If the positions of these four black spots deviate from one another to a large extent, the possibility arises of a lack of uniformity of illumination over the entire area of the fundus of the eye E. This would happen even when two of the image points, namely, $P_1$ and $P_4$ are made to coincide with each other by means known in the art.

According to the present invention, the four surfaces $R_1$ to $R_4$ are oriented in the same direction in each pair of adjacent surfaces, that is, in the front pair of surfaces $R_1$ and $R_2$, and the rear pair of surfaces $R_3$ and $R_4$, so as to bring the image points $P_1$ and $P_4$ into coincidence at a point, and the image point $P_2$ and $P_3$ into coincidence at that point. Thus the number of black spots necessary can be reduced to only one. Also provided for is the proper adjustment of the size of the spot. In the latter connection, it is to be noted that the size of the black spot can be minimized when the magnitudes of the virtual images points $P_1$ and $P_4$ of the spot are made equal to each other. To achieve this, it is required that the radii of curvature of the surfaces, $R_1$ and $R_4$ and the axial thicknesses of the constituent lenses, $d_1$, $d_2$ and $d_3$, must fulfill the following relationships:

$$|R_1| = |R_4| = d_1 + d_2 + d_3 \quad (1)$$

$$|R_2| = |R_3| = d_2 \quad (2)$$

$$d_1 = d_3 \quad (3)$$

Referring again to FIG. 2, there is shown an example of arrangement and construction of a single black spot. This single black spot 6a is provided on a transparent plate 6 located between the relay lens 5 and the ring-shaped patch 7 at a point conjugate to that point at which the four image points $P_1$ to $P_4$ coincide with one another with respect to the combination of the illuminating aperture mirror 2 and the relay lens 5. The size of the black spot 6a is found to be determined by the size of the aperture of the mirror and the magnifying power of the relay lens 5. Because the magnitudes of the virtual images $P_2$ and $P_3$ are usually smaller than those of the virtual images $P_1$ and $P_4$, the size of the black spot 6a depends upon the latter images. Further, it is not necessary to establish the exact coincidence of the positions of the virtual images, because a small deviation therefrom can be compensated for by a small increase in the size of the spot.

An example of a specific achromatic triplet may be constructed in accordance with the numerical data given in the following table for the radii, $R_1$ to $R_4$, the lens thicknesses, $d_1$ to $d_3$, along with the corresponding indices of refraction, $nd_1$ to $nd_3$, for the spectral D line of sodium, and the Abbe numbers, $Vd_1$ to $Vd_3$, of the various lenses. The minus values of the radii, $R_3$ and $R_4$, indicate surfaces concave toward the image forming incident light. Instead of using the spherical surface as $R_4$, an aspheric surface may be used. In this case, the standard spherical surface for the aspheric surface applies to the relationships.

| Focal length | f = 100 | Angle of view | 2ω = 45° |
|---|---|---|---|
| $R_1 = 95.70$ | | | |
| | $d_1 = 9.57$ | $nd_1 = 1.7552$ | $Vd_1 = 27.5$ |
| $R_2 = 76.56$ | | | |
| | $d_2 = 76.56$ | $nd_2 = 1.6170$ | $Vd_2 = 62.8$ |
| $R_3 = -76.56$ | | | |
| | $d_3 = 9.57$ | $nd_3 = 1.7552$ | $Vd_3 = 27.5$ |
| $R_4 = -95.70$ | | | |

Figure 3:
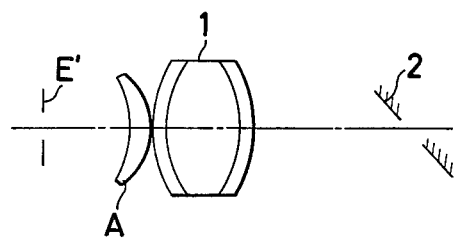
FIG. 3 is a lens block diagram showing an example of modification of the objective.

As shown in FIG. 3, the photographic objective of the present invention may include an aplanatic lens A as has already been proposed in a U.S. patent application Ser. No. 797,636 assigned to the assignee of the present invention. If so, the aplanatic lens A must be positioned in front of the triplet 1 of FIGS. 1 and 2 with the center of curvature of the front surface of lens A being in coincidence with the center of the aperture of the pupil E'. The rear surface of the lens A is an aplanatic surface.

What is claimed is:

1. An opthalmoscopic optical instrument having a wide angle of view of an object comprising;
   objective lens means having a positive refractive power and including a triplet cemented lens consisting of a negative meniscus lens convex toward the object, a biconvex lens and a negative meniscus lens concave toward the object; said triplet cemented lens having outer lens surfaces and cemented surfaces
   an image forming lens for re-imaging an image formed by said objective lens means; and
   an illuminating system having at least one light source for illumination of the object, apertured mirror for directing the illuminating light rays toward the object, and optical means for transmitting the light rays emanating from said light source to said apertured mirror, said apertured mirror being positioned on the object end of said image forming lens group; said apertured mirror being positioned between said objective lens means and said image forming lens; masking means positioned between said light source and said apertured mirror for substantially eliminating reflection from the outer lens surfaces and cemented surfaces of said triplet cemented lens; light-detecting means positioned on the image end of said image forming lens and light directing means positioned between said image forming lens group and said light-detecting means to direct the imaging light to an observing system for observation of an image of the object.

2. An ophthalmoscopic optical instrument according to claim 1, wherein said negative meniscus lens, biconvex lens, and negative meniscus lens are cemented together in the order stated.

3. An ophthalmoscopic optical instrument according to claim 2, wherein the radius of curvature of each of the outer two negative meniscus lenses is substantially equal to the sum of the axial thicknesses of the two negative meniscus lenses and the biconvex lens, and each radii of curvature of the surfaces of the biconvex lens is equal to the axial thickness of the biconvex lens.

4. An ophthalmoscopic optical instrument according to claim 1, wherein said optical means comprises a condenser lens group and a relay lens group.

5. An ophthalmoscopic optical instrument having a wide angle of view of an object comprising:

objective lens means having a positive refractive power and including a triplet cemented lens, said triplet cemented lens having a negative meniscus lens convex toward the object, a biconvex lens and a negative meniscus lens concave toward the object in the order mentioned;

an image forming lens for re-imaging an image formed by said objective lens means;

an illuminating system including at least one light source for illumination of the object, beam-reflecting means for directing the illuminating beam toward said objective lens means, and optical means for transmitting the beam emanating from said light source to said beam-reflecting means, said beam-reflecting means being positioned on the object end of said image forming lens; and masking means positioned between said light source and said beam reflecting means for preventing the reflection of light at the lens surfaces of said triplet cemented lens;

the respective radii of outer surface of said triplet cemented lens being substantially equal to the compound axial thickness of said triplet cemented lens and the respective radii of the surfaces of said biconvex lens being substantially equal to the axial thickness of said biconvex lens.

6. An ophthalmoscopic optical instrument in accordance with claim 5, wherein one of the outer surfaces of said triplet cemented lens is aspherical.

7. An ophthalmoscopic optical instrument having a wide angle of view of an eye to be inspected comprising:

objective lens means having a positive refractive power and including at least one aplanatic meniscus lens concave toward the eye and a triplet cemented lens, said triplet cemented lens including a negative meniscus lens convex toward the eye, a biconvex lens and a negative meniscus lens concave toward the object and arranged in sequence from the object, an image forming lens for re-imaging an image formed by said objective lens means, an illuminating system including at least one light source for illumination of the eye, beam-reflecting means for directing the illuminating beam toward said objective lens means, optical means for transmitting the beam emanating from said light source to said beam-reflecting and a masking means for preventing the reflection of light at the lens surfaces of said triplet cemented lens, said beam-reflecting means being positioned between said objective lens means and said image forming lens, the center of curvature of the front surface of said aplanatic meniscus lens substantially coinciding with the center of the pupil of the eye to be inspected.

* * * * *